(12) United States Patent
Bosaeus (10) Patent No.: US 9,375,357 B2
(45) Date of Patent: Jun. 28, 2016

(54) MALE INCONTINENCE GUARD

(75) Inventor: Mattias Bosaeus, Kållered (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 522 days.

(21) Appl. No.: 13/640,598

(22) PCT Filed: Apr. 14, 2010

(86) PCT No.: PCT/EP2010/054872
§ 371 (c)(1),
(2), (4) Date: Oct. 11, 2012

(87) PCT Pub. No.: WO2011/127972
PCT Pub. Date: Oct. 20, 2011

(65) Prior Publication Data
US 2013/0030403 A1    Jan. 31, 2013

(51) Int. Cl.
*A61F 13/15* (2006.01)
*A61F 13/471* (2006.01)

(52) U.S. Cl.
CPC .................................. *A61F 13/471* (2013.01)

(58) Field of Classification Search
CPC . A61F 13/471; A61F 13/4915; A61F 13/491; A61F 13/47; A61F 13/47236; A61F 13/47245; A61F 13/47254; A61F 13/475; A61F 13/4751; A61F 13/4752; A61F 13/4753; A61F 13/4755; A61F 13/4757; A61F 13/494; A61F 13/4906; A61F 13/49413; A61F 13/49453; A61F 13/49473
USPC .............. 604/385.01, 385.19, 385.24, 385.28
See application file for complete search history.

(56) References Cited

U.S. PATENT DOCUMENTS

| 5,037,417 A | 8/1991 | Ternström et al. |
| 5,401,266 A | 3/1995 | Runeman et al. |

(Continued)

FOREIGN PATENT DOCUMENTS

| EP | 1 066 006 | 1/2001 |
| EP | 1 102 678 | 5/2001 |

(Continued)

OTHER PUBLICATIONS

International Search Report (PCT/ISA/210) issued on Jul. 8, 2010, by the European Patent Office as the International Searching Authority for International Application No. PCT/EP2010/054872.

(Continued)

*Primary Examiner* — Bradley Philips
(74) *Attorney, Agent, or Firm* — Buchanan Ingersoll & Rooney PC (57) ABSTRACT

A male incontinence guard having a longitudinal extension defined between a first and a second end and a triangular base shape, the male incontinence guard comprising a liquid permeable top sheet, a liquid impermeable back sheet; an absorbent core, the absorbent core having straight longitudinal side edges; a side barrier at each longitudinal side edge of the absorbent core, each side barrier having an outer edge facing away from the respective longitudinal side edge of the absorbent core and an elastic fixed to at least the back sheet between the longitudinal side edge and the outer edge; wherein a distance between the elastics of the side barriers and the respective longitudinal side edge of the absorbent core in a direction perpendicular to the longitudinal side edge differs along the longitudinal direction.

12 Claims, 3 Drawing Sheets

(56) References Cited

U.S. PATENT DOCUMENTS

| | | | |
|---|---|---|---|
| 5,486,168 A | | 1/1996 | Runeman et al. |
| 5,651,778 A | | 7/1997 | Melius et al. |
| 5,669,896 A | * | 9/1997 | Kielpikowski ............ 604/385.28 |
| 5,752,946 A | * | 5/1998 | Boberg et al. ............ 604/385.24 |
| 6,371,950 B1 | | 4/2002 | Roslansky et al. |
| 6,402,729 B1 | * | 6/2002 | Boberg et al. ............ 604/385.28 |
| 6,440,116 B1 | * | 8/2002 | Tanji et al. ............... 604/385.19 |
| 2003/0139724 A1 | * | 7/2003 | Ragnarson et al. ...... 604/385.08 |
| 2006/0282053 A1 | * | 12/2006 | Rohrl ........................ 604/385.01 |
| 2007/0299414 A1 | * | 12/2007 | Takino et al. ................. 604/358 |
| 2012/0022487 A1 | | 1/2012 | Akiyama |

FOREIGN PATENT DOCUMENTS

| | | |
|---|---|---|
| GB | 2 289 417 A | 11/1995 |
| JP | 02-501710 A | 6/1990 |
| JP | 05-501976 A | 4/1993 |
| JP | 05-501977 A | 4/1993 |
| JP | 2011-120711 A | 6/2011 |
| RU | 2 371 157 C2 | 10/2009 |
| WO | WO 91/07155 A1 | 5/1991 |
| WO | WO 95/31164 A1 | 11/1995 |
| WO | 2004019850 | 3/2004 |

OTHER PUBLICATIONS

International Preliminary Report on Patentability (PCT/IPEA/409) issued on Feb. 3, 2012, by the European Patent Office as the International Searching Authority for International Application No. PCT/EP2010/054872.

Office Action (Notice of Reasons for Rejection) issued on Feb. 3, 2014, by the Japan Patent Office in corresponding Japanese Patent Application No. 2013-504131, and an English Translation of the Office Action. (6 pages).

Office Action (Decision on Grant) issued on Feb. 21, 2014, by the Russian Patent Office in corresponding Russian Patent Application No. 2012148251, and an English Translation of the Office Action. (10 pages).

Official Action No. 13353 issued Jul. 30, 2013 by Colombian National Patent Office in Colombian application No. 12-204403.

* cited by examiner

MALE INCONTINENCE GUARD

TECHNICAL FIELD

The present invention relates to a male incontinence guard (hereinafter referred to as male incontinence guard, incontinence guard or simply as guard). The male incontinence guard is preferably disposable, i.e. it is intended for a singular use. Further, the male incontinence guard is preferably a guard having a triangular base shape with a longitudinal extension between a first and a second end and a maximum width transverse to the longitudinal direction at the first end and a minimum width at the second end. More particular, the present invention concerns a male incontinence guard having improved side barriers preventing leakage.

BACKGROUND OF THE INVENTION

Light incontinence, i.e. a leakage of small amounts of urine, is a disability which is generally hidden and which causes sufferers to involuntarily leak urine. Although referred to as light incontinence in terms of the amount of urine leakage, it does not mean that the discomfort experienced by the person affected is insignificant. Furthermore, it is well known that the problem and its causes are different between men and women. Many men who suffer from prostate problems also suffer from light incontinence. For instance, many men who have had prostate operations have encountered problems with light incontinence.

Light incontinence is more common amongst women than amongst men, which means that incontinence guards for women are better known and there are more variants to choose from. Furthermore, the incontinence guards intended for women are customized to the female anatomy which means that these are by no means suitable for the male anatomy. Thus, due to the anatomical differences between men and women, and the differences in the nature of the incontinence, incontinence guards have been specially designed for male users.

One such incontinence guard is known from WO-A-91/07155 disclosing the features defined in the preamble of claim 1. In such an incontinence guard, elastics are fixed to a back sheet and/or a top sheet making up a chassis. The elastics are arranged between a longitudinal side edge of an absorbent core sandwiched between the back sheet and the top sheet and an outer edge of side flaps (side barriers) arranged outside the core and formed by at least the back sheet. The elastics extend parallel to the longitudinal side edge of the absorbent core and the outer edge of the side flaps and are pre-stretched primarily for curving the incontinence guard and particularly the absorbent core so as to adapt the shape of the guard to the anatomy of a male user. In the curved state, the guard adopts the shape of a bowl. In addition and because of the bending or curvature of the absorbent core, the side flaps will be upstanding in relation to the absorbent core.

Yet, it has been found by the present inventors that, although such a male incontinence guard, because of the bowl shape and the upstanding side flaps, is satisfying in regard of leakage proofness, leakage may occur even along the portions in which the side flaps are upstanding.

Further, WO-A-91/07155 discloses the possibility to remove material from the absorbent core in order to increase a distance between the outer edge of the side barriers and the side edge of the absorbent core to provide for higher sealing barriers. Yet, this, on the one hand, is disadvantageous as material is removed from the absorbent core reducing absorbency in an area where it is needed most. On the other hand, even if the barriers are higher, removing material from the absorbent core may lead to the side barriers being inclined away from the absorbent core in this area, not encapsulating the scrotum as well as desired.

Figure 4:
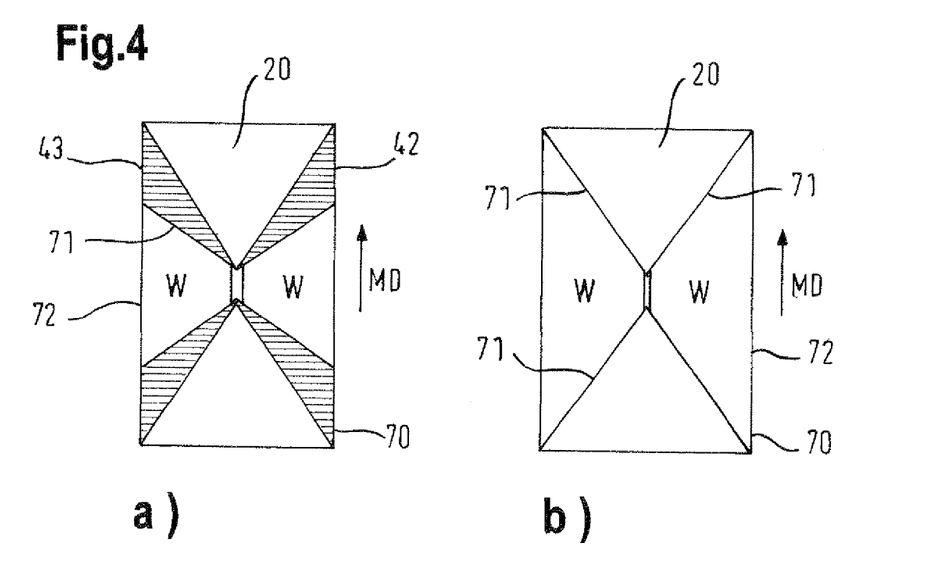

Moreover, the guard of WO-A-91/07155 may be manufactured as shown in FIG. 4b. That is, the guards are manufactured in a continuous production line with a web running in a machine direction MD as indicated in FIG. 4b. The apexes of the triangular base shape of two consecutive guards face each other in the machine direction with a distance inbetween them. Hence, the area of the continuous web being transported in the machine direction between the facing legs 71 of two consecutive guards and the longitudinal side edges 72 of the web parallel to the machine direction represent waste material W. It is an aim to reduce the waste material to a minimum.

Furthermore, an absorbent article is known from WO-A-95/31164 in which elastics in the mid-portion of the guard define an outwardly convex curved path and are connected in the end portions of the guard separated by a mid-portion to the absorbent core. The latter connection is required for providing the guard with the intended bowl shape whereas the further intends to draw up the side edges of the guard for preventing lateral leakage. However, because of the elastics in the end portions being connected to the core, the side edges of the guard do not stand up as well as intended. In addition and particularly with respect to the connection of the elastics in the top end portion, problems exist that the edges outward of the elastic fold inward limiting product function and comfort. In this context, bowl shaping especially in the top end portion of the guard is not desired.

SUMMARY OF THE INVENTION

In view of the aforesaid, it is an object of the present invention to provide a male incontinence guard having improved side barriers for preventing lateral leakage, maintaining comfort and absorbency, at the same time enabling the reduction of waste material during manufacture of the product.

This object is solved by a male incontinence guard as defined in claim 1. Particular embodiments of the present invention are defined in the dependent claims.

The basic idea of the present invention to solve this object is to provide the elastics (completely) outside of the absorbent core only, that is without any connection to the absorbent core and to configure the elastics such that a distance between the elastic and the longitudinal side edge of the absorbent core in a direction perpendicular to the longitudinal side edge is largest at a position where the side barrier needs to be highest relative to the absorbent core. This configuration prevents the male incontinence guard from bowl shaping in the region of the first end, improving comfort, at the same time enabling raising the side barriers in relation to the planar extension of the absorbent core. Further, this configuration enables more material of the web in the manufacturing process being used in the final product reducing the amount of waste material W.

Accordingly, the present invention suggests a male incontinence guard having a longitudinal extension defined between a first and second end and a (triangular base) shape in use with a maximum width transverse to the longitudinal direction at the first end and a minimum width at the second end. It is to be understood that "triangular base shape" also encompasses triangles having rounded corners and even triangles the apex of which is cut, forming an equal-sided trapezoid. Also triangles with non-linear circumferential edges are conceivable.

The male incontinence guard of the present invention comprises a liquid permeable top sheet. The top sheet is that sheet which in use of the guard is in contact with the skin of the wearer or at least facing the skin. The liquid permeable layer may suitably be made of a non-woven material. Another conceivable material is perforated plastic. In particular, the material of the top sheet is preferably selected from a material that exhibits characteristics such as dryness and softness when the guard is being worn. It is also desirable for the top sheet to be non-irritating to the skin and to have a soft and textile-like surface which remains dry even in the event of repeated wetting. The top sheet could consist of a non-woven material, e.g. a spunbond nonwoven material, a carded nonwoven material, an air-thru nonwoven material, a spunlace nonwoven (hydroentangled) material, a meltblown nonwoven material, a wetlaid nonwoven material, or a combination of these. Said nonwoven material could be based on either natural fibres such as cellulose or cotton, or alternatively on synthetic fibres such as for example polypropylene (PP), polyethylene (PE) polyester (PET), polyamide (PA), or a combination of these. If a combination is used, this could be a mixture of fibres from different natural and/or synthetic polymers, although each fibre can also contain different polymers (for example PP/PE bi-component fibres or PP/PE copolymers). The topsheet could also be a perforated, hydrophobic nonwoven material in order to keep the surface which is closest to the user's body dry. Additionally, the holes of said perforated, hydrophobic nonwoven material impart a textile-like and comfortable feel to the topsheet. The diameter of the holes of such a perforated, hydrophobic nonwoven material is larger than the distance between the fibres in the material. In this way, liquid can be led down through the holes in the topsheet to the subjacent absorption core. The skilled person will understand how the holes in the perforated, hydrophobic nonwoven material may be adjusted depending on the intake properties and the type of absorbent article which is to be produced. The liquid-permeable topsheet could also comprise several layers of material, i.e. a laminate. Such a laminate could for example comprise a first and a second layer of material. The laminate could also alternatively consist of the same material or a combination of the following materials: perforated film/nonwoven, perforated film/perforated film, nonwoven/nonwoven, perforated nonwoven/nonwoven, and perforated nonwoven/perforated nonwoven. Herein, it is understood that the first layer of material is the layer which is intended to be facing the user, and the second layer of material is subjacent the first layer of material. The laminate could be fully or partially perforated. That is to say, holes could be made in the first layer, second layer or in both the first and second layers. The guard could also be perforated solely in the central portion or in the full extent of the guard. The layers of the laminate could be joined together by means of gluing, or welding by ultrasonic bonding or laser, or by mechanical joining, for example in the form of embossing or compression, etc. or by some other appropriate method of joining, for example by thermal bonding. Reference is made to the entire content of EP 1 066 006 B1 and EP 1 102 678 B1, both disclosing suitable materials and combinations of materials which are suitable for a laminate, and also disclosing a method for preparing a suitable laminate for the use as a topsheet. The topsheet could also be made from renewable raw materials. An example of such a topsheet based on renewable raw materials is TERCOT 20, commercially available from Fiberweb. One preferred example of a suitable material for the topsheet is a 18 g/m² spunbond nonwoven from Union, available under the trade name S1800 PPW.

The male incontinence guard of the present invention further comprises a liquid impermeable back sheet. The back sheet could consist of a plastic film, e.g. a polyethylene or polypropylene film, a non-woven material which for example could be treated with a liquid impervious material or a hydrophobic non-woven material which resists liquid penetration, or a laminate comprising plastic films and nonwoven materials. Other types of liquid barrier materials could also be used as liquid-impermeable backsheets, such as e.g. closed-cell plastic foams or various liquid barrier laminates. It is preferred that the backsheet is permeable to air and vapour so as to allow vapour to escape from the absorbent core, while still preventing liquids from passing therethrough. Examples of breathable backsheet materials are porous polymeric films, nonwoven laminates from spunbond and meltblown layers, laminates from porous polymeric films and nonwovens. The backsheet could also be made from renewable materials. Examples of such backsheets are Bio-Air, a plastic film commercially available from Nuova Pansac, and PLA/PP Bico 50/50, a non-woven material commercially available from Fiberweb. One preferred example of a suitable material for the backsheet is a 25 g/m² nonwoven/plastic laminate from Trioplanex, available under the trade name W14Ma11.

Further, there is provided an absorbent core between the top sheet and the back sheet. At least a part of the back sheet extends beyond the circumference of the absorbent core. Yet, it is preferred that preferably at least a part of both the top sheet and the back sheet extend beyond the circumference and particularly the longitudinal side edges of the absorbent core. Even more preferred, both the top sheet and the back sheet may have a somewhat greater extension in the plane than the absorbent core and extend beyond the outer edges of the absorbent core. The top sheet and the back sheet may be connected to each other within the projecting portions thereof. Joining can take place by gluing, or by welding by means of ultrasound or a laser, or by mechanical joining, for example in the form of embossing or compression, etc. or by some other appropriate method of joining, for example by thermal bonding.

The absorbent core may as well have a triangular base shape with straight longitudinal side edges. The term triangular does encompass the same shapes as indicated above with respect to the triangular base shape of the male incontinence guard. More generally spoken, the term "triangular" encompasses all shapes in which the longitudinal edges diverge from the second narrow end to the first wide end. Accordingly, the longitudinal side edges of the absorbent core may be non-parallel. Contrary to the circumferential edges of the guard, the legs of the triangular base shape of the core, i.e. the longitudinal side edges of the absorbent core are straight. The absorbent core can be of any conventional kind. Examples of commonly-occurring absorbent materials are cellulosic fluff pulp, tissue layers, highly absorbent polymers, so-called super absorbent polymers (SAP), absorbent foam materials, absorbent nonwovens or the like. SAP are water-swellable, water-insoluble organic or inorganic materials capable of absorbing at least about 10 times their weight as according to ISO 17190-6 "Gravimetric determination of fluid retention capacity in saline solution after centrifugation". Organic materials suitable for use as a superabsorbent material include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Preferred superabsorbent materials are further surface crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like. It is common to combine cellulosic fluff pulp with superabsorbents in an absorbent core. It is also common to have absorbent cores comprising layers of different materials with different properties with respect to liquid acquisition capacity, liquid distribution capacity and storage capacity. The thin absorbent cores which are common in incontinence guards often comprise a compressed mixed or layered structure of cellulosic fluff pulp and superabsorbents. For example, the absorbent core material could comprise an upper absorbent core and a lower absorbent core. The term "upper" as used herein relates to the portion of the product intended to be positioned closer to the user when in use, whereas the term "lower" as used herein relates to the portion of the product closer to the garment-facing surface thereof. Furthermore, SAP in the lower absorbent core has the main function of increasing the liquid storing capacity of this layer whereas the main function of SAP in the upper absorbent core is to prevent rewetting of liquid absorbed in this layer if the article is compressed by external forces during use. The SAP in the upper absorbent core could be of a different type than the SAP used in the lower absorbent core or be present in a lower percentage than in the lower absorbent core. The SAP may be applied in localised areas of an absorbent core, e.g. in intake regions, liquid distribution regions and/or liquid retention regions. The person skilled in the art will understand how the concentration of SAP in an absorbent core may be adjusted depending on the absorbent properties and the type of absorbent article which is to be produced, e.g. a high amount of SAP may be used in order to achieve a thin absorbent article, while lower amounts may be used in some hygiene articles intended for light incontinence products. One preferable example of a suitable material for the absorbent core is pulp mixed with approximately 30% of SAP from BASF, Ludwigshafen, Germany available under the trade name Hysorb M7125. The mixture of cellulose fluff and SAP has preferably a density of 0.08-0.13 g/cm3. The absorbent core may also be made from a chlorine-free fluff pulp such as Totally Chlorine Free fluff pulp which is commercially available from Stora Enso.

Beside the absorbent core, the guard may also comprise other layers such as a fluid acquisition layer for a quick transport of body fluids. The fluid acquisition layer has an open porous structure and should be able to quickly receive and temporarily store a certain amount of fluid and transfer it further to the underlying absorbent core. This is important, especially for the thin, compressed absorbent articles of today, which often have a high content of SAP. Absorbent articles of today certainly have high absorption capacity, but on the other hand they sometimes have a receiving speed which is too low to instantaneously cope with receiving large amounts of liquid which could be released upon urination within a few seconds time interval. The fluid acquisition layer is usually a so-called high loft material produced by carding and through-air bonding or needling synthetic fibres, such as polyester, polypropylene or mixtures thereof. A suitable material for the acquisition layer is a hydrophobic wadding of through air nonwoven available from LIBELTEX, having the trade name DRY WEB T 23W.

In addition and according to the present invention, there is provided a side barrier at each longitudinal side edge of the absorbent core. The side barrier may be formed by at least the back sheet or at least the back sheet and the top sheet. In this context, a portion of the back sheet or the back sheet and the top sheet extends beyond at least a longitudinal portion of the longitudinal side edges of the absorbent core form the side barrier. In other words, the side barrier consists of this portion or these portions only.

Each side barrier has an outer edge which faces away from the respective longitudinal side edge of the absorbent core and an elastic which is fixed to at least the back sheet. The elastic may as well be fixed to the back sheet and the top sheet. Yet, the elastic is not fixed to the absorbent core. In addition, the elastic is not disposed over the core. In other words, the elastic is disposed between the longitudinal side edge of the absorbent core and the outer edge of the side barrier only. The pre-stretched elastics, preferably of mutually equal lengths, may, for instance, be in the form of elastic threads, bands or the like. The use of elastic foam material is also conceivable. The elastics could be glued to one or to both of the topsheet or backsheet. Methods of applying elastics to hygiene products are well-known to the person skilled in the art. In one preferred embodiment the elastics may be placed within 10 mm from the first and second end. The elastics help the guard to form a basin(bowl)-like shape which encloses the genitals of the user, thereby helping to maintain a close fit of the guard.

The present invention is characterized in that a distance between the elastics of the side barriers and the respective longitudinal side edge of the absorbent core in a direction perpendicular to the longitudinal side edge differs along the longitudinal direction. Where distance between the elastics and the respective longitudinal side edge of the absorbent core is largest, the side barrier may stand up highest with respect to the side edge of the absorbent core, thereby preventing lateral leakage. At the same time, an improved comfort may be obtained because no bowl shaping takes place in the vicinity of the first end as the elastics are not disposed over the absorbent core at all and particularly not in the vicinity of this end. Furthermore and if the elastics are more distant from the longitudinal side edge of the absorbent core, more material in the traverse direction is required for forming the side barrier, whereby the waste material in the manufacturing process may be reduced (see later explanations with respect to FIG. 4a).

In order not to increase the width of the web material from which the male incontinence guard is manufactured, transverse to the machine direction, that is in cross-machine direction, it is preferred that the outer edges of the side barriers reside on or within the maximum width of the guard. Thereby, the material required to manufacture the male incontinence guard of the present invention and compared to a male incontinence guard of the prior art as shown in WO-A-91/07155 is not increased when comparing incontinence guard with the same dimensions in regard of the maximum width at the first end. Thereby a more efficient use of material is enabled.

According to an embodiment of the invention, the elastics substantially follow the run of the outer edge of the respective side barrier. In general, the distance between the elastic and the outer edge is substantially constant in the longitudinal direction. In other words, it is preferred that the extension of the elastic and the extension of the outer edge are parallel. Yet, because of the manufacturing process the distance may change in the longitudinal direction. In this context, the term "substantially" should also encompass embodiments, where a deviation from the exact parallel orientation of the elastics to the outer edges is less than 15%, preferably less than 10% and even more preferred less than 5%. If the outer edge has a wave shape, the run of the outer edge is not the wave shape, but an approximation.

In this context, the distance between the outer edges of the side barriers and the respective longitudinal side edges of the absorbent core in a direction perpendicular to the longitudinal side edge may as well differ along the longitudinal direction.

According to a particular embodiment of the present invention and enabling the maintenance of a simple manufacturing process, the elastics of the side barriers and/or the outer edges of the side barriers have a first portion extending substantially parallel to the longitudinal extension of the male incontinence guard and a second portion extending from the first portion toward a longitudinal center axis of the male incontinence guard. It is particularly preferred that the portion extending substantially parallel to the longitudinal extension of the male incontinence guard is located at the first end, whereas the other portion extending from the first portion toward the longitudinal center axis is disposed at the second end portion. Thereby, it may be achieved that when cutting the male incontinence guard from the web in the continuous manufacturing process, the same number of cuts are necessary as in a case in which the elastics and/or the outer edges of the side barriers extends parallel to the longitudinal side edges of the absorbent core. According to one embodiment, the first portion extend from the vicinity of the transverse edge at the first end towards a position, where the distance between the outer edge of the side barrier and/or the elastic to the longitudinal side edge of the core is largest and the second portion extends from there to the vicinity of the transverse edge at the second end.

Moreover and as previously mentioned, it is preferred that the elastics extend from a position at which the distance between the elastics and the corresponding longitudinal side edge is largest, that is from a position where most lateral leakage is to be expected, towards the first and second end where the distance is smallest.

Further, it is preferred according to the present invention that the elastics extend from the first end toward the second end to in the use position draw the first end and the second end of the male incontinence guard together to shape the male incontinence guard to a bowl.

It has been found by the present inventors that lateral leakage is generally expected in a mid-portion, that is an intermediate portion between the first and second end portion of a product. In this context, it has been found that it is preferred that the distance is largest at a position in between 2:30 and 5:00 o'clock, preferably 3:00 and 4:30 o'clock at one longitudinal side and 7:00 and 09:30 o'clock, preferably 7:30 and 09:00 o'clock at the opposite longitudinal side with a wetting point on a longitudinal center line being the center and the first end defining 12:00 o'clock and the second end defining 6:00 o'clock. In this context, the wetting point is selected on a longitudinal center line based by experiments explained later on with respect to the FIG. 3.

To achieve this, it may be preferred that the elastics are convex curved away from the longitudinal side edges of the absorbent core with the apex of the convex curve at the position where most leakage is to be expected. Alternatively, the elastics diverge from that position towards the first and second end where the distance is smallest. That is, the elastics have two more or less linear portions which intersect each other at an angle. The point of intersection is the point from which the elastics diverge toward the first and second end and where the distance is largest. Yet, it is also conceivable to combine these embodiments in that straight portions of the elastics are connected by a curved elastic or a plurality of substantially linear portions are connected to each other to form a substantially curved elastic.

Even further features and advantages of the present invention which may be incorporated separate from one or more of the above features or in combination therewith, unless the features contradict each other are explained in the following description of a preferred embodiment of the present invention.

BRIEF DESCRIPTION OF THE FIGURES

This description makes reference to the accompanying drawings, in which:

FIG. 4*a* a cutout from a manufacturing process of the guard according to the present invention and FIG. 4*b* a corresponding cutout concerning the possible manufacture of a guard as disclosed in WO 91/07155.

DETAILED DESCRIPTION OF THE PREFERRED EMBODIMENTS

In the following, the embodiments of the present invention will be described in further detail with reference to the illustrative Figures as attached hereto.

Figure 1:
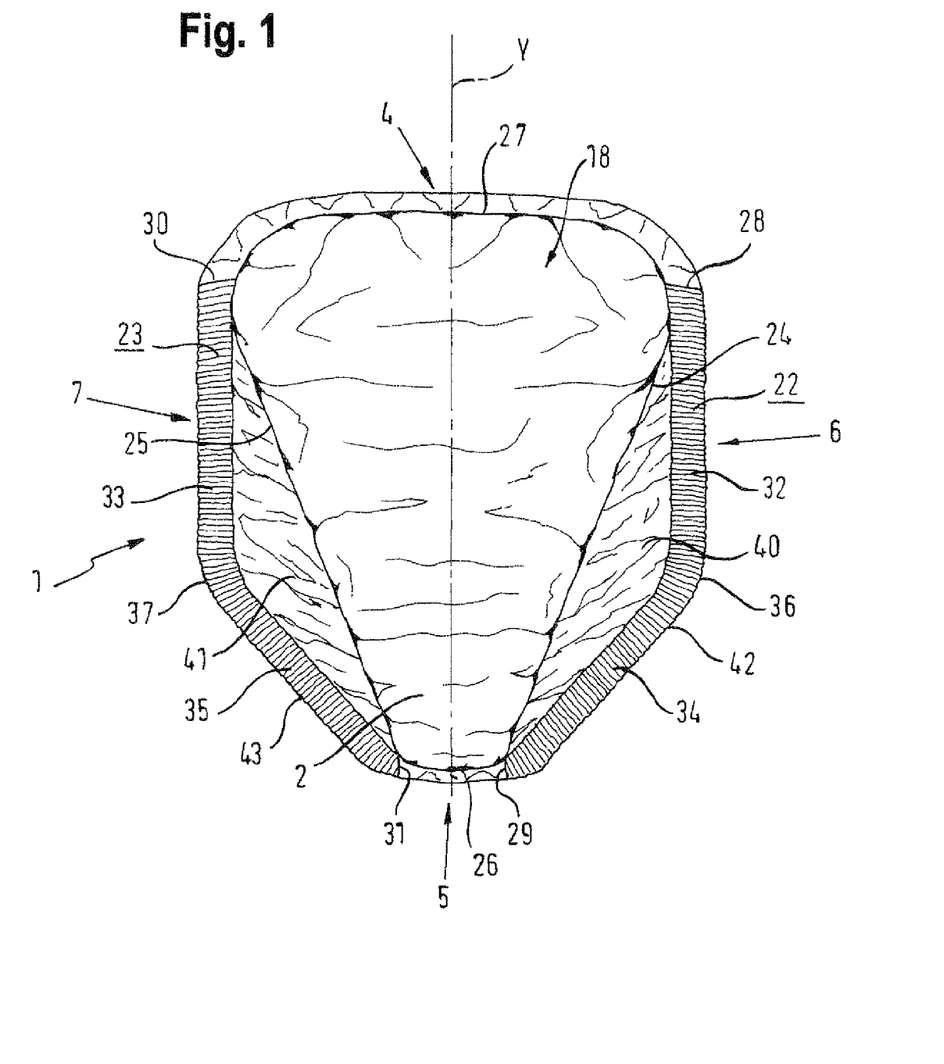
FIG. 1 shows a plan view of a male incontinence guard according to the present invention in a flattened state with the top sheet being directed upwards.
Figure 2:
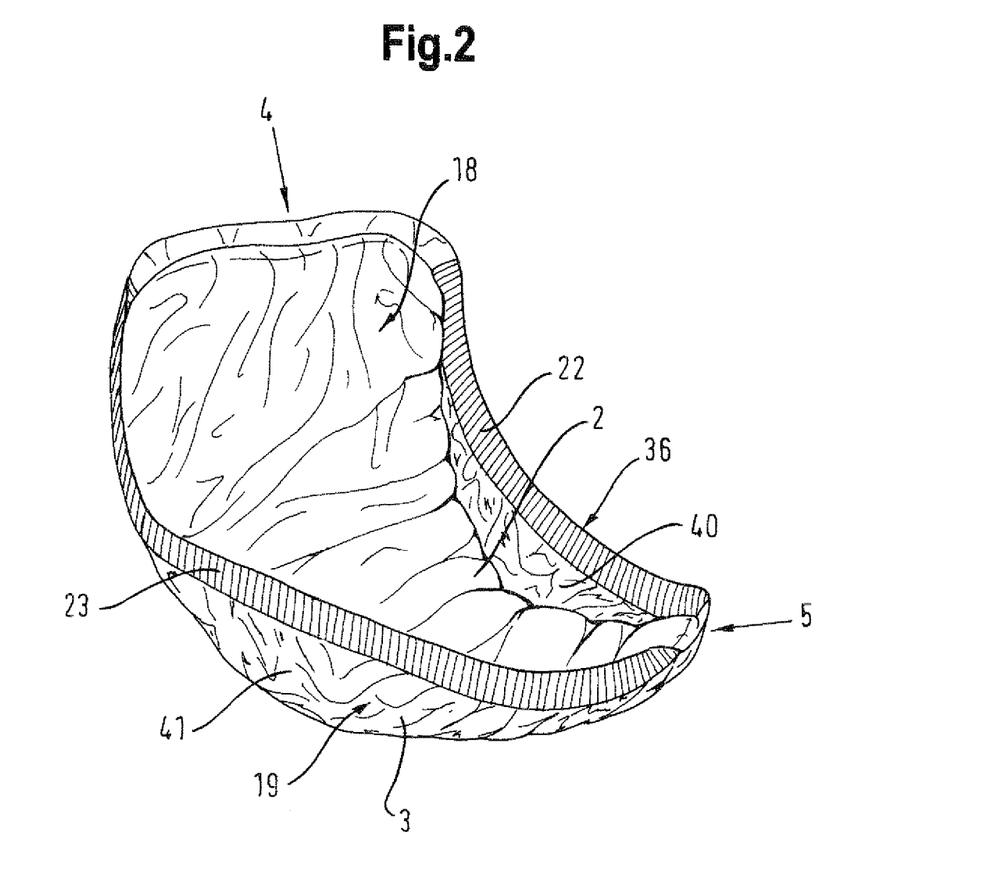
FIG. 2 a perspective view of the incontinence guard as shown in FIG. 1 in the bowl shape.

As illustrated in FIGS. 1 and 2, a male incontinence guard 1 is shown which comprises a liquid-permeable topsheet 18, a backsheet 19, which preferably is liquid-impermeable, and an absorbent core 20 (FIGS. 3 and 4) located therebetween. The guard 1 may furthermore comprise a not shown fluid acquisition layer located between said topsheet 18 and said absorbent core 20.

The guard 1 has a body-facing surface 2, which is the surface that makes contact with the user when the guard 1 is being worn. The guard 1 has a garment-facing surface 3, which is the surface that makes contact with the garment of the user when the guard is being worn. Typically, the body-facing surface 2 of the guard 1 comprises (or consists of) the topsheet 18, while the garment-facing surface 3 comprises (or consists of) the backsheet 19.

The topsheet 18 and the backsheet 19 of the male incontinence guard 1 preferably have a somewhat greater extension in the plane than the absorbent core 20 and the acquisition layer, and extend outside the edges thereof. The topsheet 18 and the backsheet 19 are connected to each other within the projecting portions thereof.

With regard to the geometrical shape of the male incontinence guard 1 of the present invention, a preferred shape of the guard is illustrated in e.g. FIG. 1. As schematically illustrated, the guard 1 has a front transverse edge (first end) 4, intended to be located forward on the user, a rear transverse edge (second end) 5, intended to be located rearward on the user, and at least two longitudinal side edges 6,7 extending between the front transverse edge 4 and the rear transverse edge 5. The guard 1 preferably tapers towards the rear transverse edge 5, i.e. the front transverse edge 4 is longer than the rear transverse edge 5. The tapered shape allows the guard 1 to fit comfortably in the crotch region of a male user. Thus, the male incontinence guard 1 of the present invention may be essentially isosceles trapezoid having a triangular base shape in use, when being shaped like a bowl. Herein the term "isosceles trapezoid" is a quadrangle with a line of symmetry bisecting one pair of opposite sides, making it automatically a trapezoid. In other words, the front and rear transverse edges 4,5 are substantially parallel to each other, and the longitudinal side edges 6,7 are of equal length. The diagonals are also of equal length. An isosceles trapezoid's base angles are congruent, i.e. it has corresponding sides and angles that are equal. The expression essentially isosceles trapezoid in this context means that, for instance, the corners of the essentially isosceles trapezoid may be rounded or that the edges 4,5,6 and/or 7 of the male incontinence guard 1 may not be completely linear, but that the guard has the general form as described above. In another alternative embodiment the geometrical shape of the guard 1 may be T-shaped. According to such an embodiment the longitudinal side edges 6, 7 may include one or several angles of different directions. According to the present invention and as shown in FIG. 1, the elastics 22, 23 on both sides of the longitudinal center line have a distance to the longitudinal side edges 24, 25 of the absorbent core. The elastics have two opposite ends 28, 29 and 30, 31, one end 28, 30 is connected to the top sheet 18 and the back sheet in the vicinity of the first end 4 whereas the opposite end 29, 31 is connected to the top sheet 18 and the back sheet 20 in the vicinity of a second end 5. In the depicted embodiment, the elastics 22, 23 are formed by an elastic foam material which increases comfort compared to elastic threads or bands which are shown as alternative schematically in FIG. 3.

The elastics 22, 23 between their ends 28, 29 and 30, 31 are constituted by a first portion 32, 33 and a second portion 34, 35. As shown in FIG. 1, the first portion 32, 33 extends substantially parallel to the longitudinal center line y whereas the second portion 34, 35 extends from the first portion 32, 33 towards the longitudinal center axis y and the second end 5. The first portion 32, 33 is connected at the first end 4 and the second portion 34, 35 is connected at the second end 5. In the depicted embodiment, the portions 32, 34 and 33, 35 each have a substantially linear extension connected by a curved portion 36, 37. At the curved portion 36, 37 the distance between the elastics 32, 33 and the longitudinal outer edges 24, 25 of the absorbent core is largest. That is, at this position resides the apex of the convexly curved extension of the elastics 22, 23. The elastics 22, 23 may be one piece elastics. However, it is as well conceivable to form the elastics from a plurality of pieces. For example, the first portion 32 may be one piece and the portion 34 may be another piece. In addition, there does not need to be a curved portion 36 between the portions, but the portions 32, 34 or the pieces if constituted by separate piece may intersect each other under a particular angle, wherein the portions/pieces diverge from the point of intersection which would equal the curved portion 36. As shown in FIG. 1, the elastics 22 and 23 follow the extension (run) of the outer edges 42, 43 of the side barriers 40, 41 and, hence, have an extension parallel to the extension of these outer edges.

Considering FIG. 2 showing the guard of FIG. 1 in use, it becomes apparent that the elastics 22, 23 pull the first end 4 and the second end 5 together to provide for bowl shape. In this illustration, the side barriers 40, 41 formed from the top sheet 18 and the back sheet 19 are highest in the region of the curved portion 36.

The position of the curved portion 36 or in other words the position where the distance between the elastics 22, 23 is largest to the longitudinal outer edges 24, 25 of the absorbent core will be selected based on an experiment indicating at which portions lateral leakage most likely occurs. First, a plurality of used (test users) incontinence guards is investigated. In this investigation, the area of the absorbent core of the product is diverted into a plurality of squares having a side length of 10 mm (see FIG. 3). Subsequently, the used product is visually analyzed to determine which square contains urine. Each square reflects in term of percentage the number of products that showed urine in that particular square. That is, the more of the products showed urine in a square, the higher the percentage. Hence, FIG. 3 reflects the probability of a product being wet in that particular area. That square on the longitudinal center line y with the highest percentage of products which showed urine in that square is selected as the wetting point and forms the center of a clock, wherein the first end defines 12 o'clock and the second defines 6 o'clock.

Figure 3:
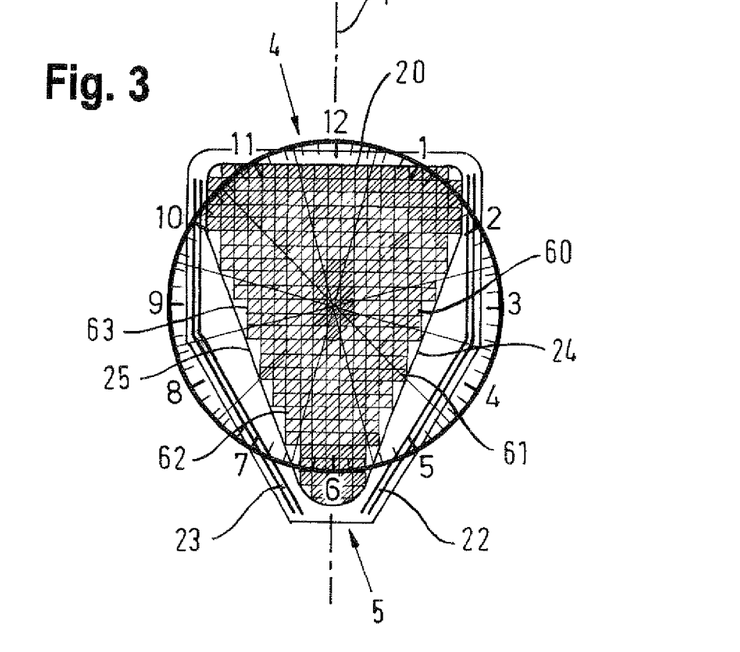
FIG. 3 a schematic plan view similar to that of FIG. 1 showing the likelihood of lateral leakage.

As shown in FIG. 3, the squares over the planar extension of the absorbent core indicate the percentage of products which showed urine in that square. The present inventors concluded on this experiment, that the squares 60 and 61 and 62 and 63 out of the squares at the outer circumferential edge of the absorbent core 20 indicated the highest percentage. As a result, lateral leakage in most cases will occur along this portion of the longitudinal side edges 24, 25 of the absorbent core 20 so that the elastics 22, 23 should be most distant to the longitudinal side edges 24, 25 of the absorbent core 20 between these squares. Hence, it is preferred that the elastics are most distant between 2:30 and 5 o'clock, preferably 3 to 4:30 on the right hand side in FIG. 3 and between 7 and 9:30 o'clock, preferably 7:30 and 9 o'clock on the left hand side in FIG. 3.

Finally, an explanation is being given regarding a possible process for manufacturing the product as shown in FIGS. 1 and 2. In this context, it is preferred that a continuous web 70 is continuously transported in a machine direction MD, wherein the web material 70 represents the back sheet and/or top sheet material. During manufacture, the absorbent core 20 is placed upon the web 70 and encapsulated between the top sheet and the back sheet. Subsequently, the elastics (not shown in FIG. 4) are applied by known methods as aforesaid. In a final step, the products are cut from the web 70 to form the final product.

As shown in FIG. 4b considering the corresponding process of a known product, the areas W of the web 70 are waste material which, after the cutting process, is not part of the product. These areas are much larger than in FIG. 4a. Hence, the waste material W in the manufacturing process of the male incontinence guard according to the present invention is reduced. As a portion of the outer edges 42, 43 of the side barriers 40, 41 extends parallel to the longitudinal direction, this may be formed by the longitudinal edges 72 of the web 70 in the machine direction so that no cutting process is required in regard of these edges.

Hence, the process of manufacturing the product is still as simple as in the prior art but uses more material than the prior art product. To put it differently, a material web having a certain width is required for manufacturing both a prior art product and a product of the present invention having the same maximum width at one of their ends. This material web is, hence, the same for the product of the invention and the prior art product. However, more of the material web constitutes the product of the invention than the prior art product. Hence, the present invention makes more effective use of this material.

The above description of a particular embodiment is only exemplary and various modifications will be apparent to the skilled person. Therefore, the present invention should not be limited by the above embodiment and the enclosed figures. Rather, the scope of protection is determined by the following claims.

The invention claimed is:

1. A male incontinence guard having a longitudinal extension defined between a first and a second end, and a periphery of the incontinence guard in a flattened state having a maximum width transverse to the longitudinal direction at the first end and a minimum width at a longitudinally outermost edge of the incontinence guard at the second end, the maximum width being larger than the minimum width, the male incontinence guard comprising:
   a liquid permeable top sheet;
   a liquid impermeable back sheet;
   an absorbent core between the top sheet and the back sheet, the absorbent core having a triangular base shape with straight longitudinal side edges; and
   a side barrier at each longitudinal side edge of the absorbent core, each side barrier being formed by at least the back sheet extending beyond at least a longitudinal portion of a respective one of the longitudinal side edges of the absorbent core, each side barrier having a respective outer edge facing away from the respective one of the longitudinal side edges of the absorbent core and an elastic fixed to at least the back sheet in an area between the respective one of the longitudinal side edges and the respective outer edge, wherein the elastics extend only in the area between the respective one of the longitudinal side edges and the respective outer edge;
   wherein:
   a distance between the elastics of the side barriers and the respective longitudinal side edges of the absorbent core in a direction perpendicular to the longitudinal side edge differs along the longitudinal direction, wherein the elastics each extend from a position at which the distance between the elastics and the corresponding longitudinal side edges is largest towards the first and second ends where the distance is smallest.

2. The male incontinence guard as set forth in claim 1, wherein the elastics substantially follow a run of the respective outer edge of the respective side barrier.

3. The male incontinence guard as set forth in claim 1, wherein the distance between the outer edges of the side barriers and the respective longitudinal side edges of the absorbent core in a direction perpendicular to the longitudinal side edges differs along the longitudinal direction.

4. The male incontinence guard as set forth in claim 1, wherein the elastics of the side barriers and/or the outer edges of the side barriers have a first portion extending substantially parallel to the longitudinal extension of the male incontinence guard and a portion extending from the first portion toward a longitudinal center axis of the male incontinence guard.

5. The male incontinence guard as set forth in claim 1, wherein the distance is largest at a position in between 2:30 and 5:00 o'clock at one longitudinal side edge and 7:00 and 09:30 o'clock, at the opposite longitudinal side edge with a wetting point on a longitudinal center line being the clock center and the first end defining 12:00 o'clock and the second end defining 6:00 o'clock.

6. The male incontinence guard as set forth in claim 1, wherein the elastics are convex curved away from the longitudinal side edges of the absorbent core.

7. The male incontinence guard as set forth in claim 1, wherein the elastics diverge from a position at which the distance between the elastics and the corresponding longitudinal side edges is largest towards the first and second end where the distance is smallest.

8. The male incontinence guard as set forth in claim 1, wherein the side barriers are formed by the back sheet and the top sheet.

9. The male incontinence guard as set forth in claim 1, wherein the distance is largest at a position in between 3:00 and 4:30 o'clock at one longitudinal side edge and 7:30 and 09:00 o'clock at the opposite longitudinal side edge with a wetting point on a longitudinal center line being the clock center and the first end defining 12:00 o'clock and the second end defining 6:00 o'clock.

10. The male incontinence guard as set forth in claim 1, wherein the male incontinence guard has a triangular base shape.

11. The male incontinence guard as set forth in claim 1, wherein a distance between the longitudinal side edges increases in a direction from the second end toward the first end, so that the longitudinal side edges define a tapering shape.

12. A male incontinence guard having a longitudinal extension defined between a first and a second end, and a periphery of the incontinence guard in a flattened state having a maximum width transverse to the longitudinal direction at the first end and a minimum width at a longitudinally outermost edge of the incontinence guard at the second end, the maximum width being larger than the minimum width, the male incontinence guard comprising:
   a liquid permeable top sheet;
   a liquid impermeable back sheet;
   an absorbent core between the top sheet and the back sheet, the absorbent core having a triangular base shape with straight longitudinal side edges; and
   a side barrier at each longitudinal side edge of the absorbent core, each side barrier being formed by at least the back sheet extending beyond at least a longitudinal portion of a respective one of the longitudinal side edges of the absorbent core, each side barrier having a respective outer edge facing away from the respective one of the longitudinal side edges of the absorbent core and an elastic fixed to at least the back sheet in an area between the respective one of the longitudinal side edges and the respective outer edge, wherein the elastics do not overlap any part of the core;
   wherein:
   a distance between the elastics of the side barriers and the respective longitudinal side edges of the absorbent core in a direction perpendicular to the longitudinal side edge differs along the longitudinal direction, wherein the elastics each extend from a position at which the distance between the elastics and the corresponding longitudinal side edges is largest towards the first and second ends where the distance is smallest.

* * * * *